(12) United States Patent
Koehler et al.

(10) Patent No.: US 11,796,484 B2
(45) Date of Patent: Oct. 24, 2023

(54) APPARATUS FOR PROCESSING DATA ACQUIRED BY A DARK-FIELD AND/OR PHASE CONTRAST X-RAY IMAGING SYSTEM

(71) Applicant: KONINKLIJKE PHILIPS N.V., Eindhoven (NL)

(72) Inventors: Thomas Koehler, Norderstedt (DE); Klaus Jürgen Engel, Veldhoven (NL); (Continued)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 42 days.

(21) Appl. No.: 17/633,223

(22) PCT Filed: May 26, 2021

(86) PCT No.: PCT/EP2021/063949
§ 371 (c)(1),
(2) Date: Feb. 7, 2022

(87) PCT Pub. No.: WO2021/249769
PCT Pub. Date: Dec. 16, 2021

(65) Prior Publication Data
US 2023/0105815 A1 Apr. 6, 2023

(30) Foreign Application Priority Data
Jun. 9, 2020 (EP) ........................ 20178885

(51) Int. Cl.
*G01N 23/20* (2018.01)
*G01N 23/041* (2018.01)
*G06T 7/80* (2017.01)

(52) U.S. Cl.
CPC ............... *G01N 23/041* (2018.02); *G06T 7/80* (2017.01); *G01N 2223/401* (2013.01);
(Continued)

(58) Field of Classification Search
None
See application file for complete search history.

(56) References Cited

U.S. PATENT DOCUMENTS 7,177,390 B2  2/2007  Martin et al.
9,959,640 B2  5/2018  Koehler et al.
(Continued)

FOREIGN PATENT DOCUMENTS

WO  2008029107 A2  3/2008

OTHER PUBLICATIONS

Koehler T. et al., "Non-Scatter Contributions to the Dark-Field Signal in Differential Phase Contrast Imaging", AIP Conference Proceedings, Jul. 31, 2012, pages 205-210.
(Continued)

*Primary Examiner* — Hoon K Song
(74) *Attorney, Agent, or Firm* — Larry Liberchuk (57) ABSTRACT

The present invention relates to an apparatus (10) for processing of data acquired by a dark-field and/or phase contrast X-ray imaging system, the apparatus comprising an input unit (20), and a processing unit (30). The input unit is configured to provide the processing unit with blank scan fringe data acquired by a dark-field and/or phase contrast X-ray imaging system comprising an interferometry arrangement and detector. The input unit is configured to provide the processing unit with sample scan fringe data acquired by the dark-field and/or phase contrast X-ray imaging system, with an object to be imaged is positioned within the dark-field and/or phase contrast X-ray imaging system. The processing unit is configured to pre-process the blank scan fringe data to determine pre- processed blank scan fringe data comprising utilization of an effective point spread function "PSF". The processing unit is configured to pre-process the sample scan fringe data to determine pre- processed sample scan fringe data, comprising utiliza-
(Continued)

tion of the effective point spread function "PSF". The effective PSF has been determined for the dark-field and/ or phase contrast X-ray imaging system.

14 Claims, 7 Drawing Sheets

(72) Inventors: Franz Josef Pfeiffer, Unterföhring (DE); Theresa Urban, Garching (DE)

(52) U.S. Cl.
CPC ................... *G06T 2207/10116* (2013.01); *G06T 2207/30061* (2013.01)

(56) References Cited

U.S. PATENT DOCUMENTS

| | | |
|---|---|---|
| 10,393,681 B2 | 8/2019 | Handa |
| 10,417,761 B2 | 9/2019 | Koehler et al. |
| 10,896,485 B2 | 1/2021 | Maack |
| 2014/0233697 A1 | 8/2014 | Ignatyev et al. |
| 2016/0109387 A1 | 4/2016 | Pan |
| 2016/0356730 A1* | 12/2016 | Handa .................... G21K 1/02 |
| 2019/0159742 A1* | 5/2019 | Behling ................. A61B 6/502 |
| 2020/0330059 A1* | 10/2020 | Fredenberg et al. . A61B 6/4291 |

OTHER PUBLICATIONS

PCT International Search Report, International application No. PCT/EP2021/063949, Aug. 6, 2021.

Weitkamp T. Al. , "X-Ray Phase Imaging with a Grating Interferometer", Optics Express, vol. 13, No. 16, Aug. 2005, pages 6296-6304.

\* cited by examiner

APPARATUS FOR PROCESSING DATA ACQUIRED BY A DARK-FIELD AND/OR PHASE CONTRAST X-RAY IMAGING SYSTEM

FIELD OF THE INVENTION

The present invention relates to an apparatus for processing of data acquired by a dark-field and/or phase contrast X-ray imaging system, to a system for dark-field or phase contrast X-ray imaging, to a method for processing of data acquired by a dark-field and/or phase contrast X-ray imaging system, as well as to a computer program element and a computer readable medium.

BACKGROUND OF THE INVENTION

Differential phase contrast and dark-field imaging are promising technologies that will likely enhance the diagnostic quality of X-ray Computer Tomography (CT) and X-ray radiography systems. X-ray dark-field and phase contrast imaging has demonstrated a high potential for an improved diagnosis of pulmonary disorders. Dark-field imaging is expected to provide additional diagnostic information in particular in chest imaging for the assessment of lung diseases. Several pre-clinical studies demonstrated this, for instance for the detection of emphysema, fibrosis, pneumothorax, and lung cancer. X-ray dark-field imaging, for example, quantifies the small-angle scattering that is occurring in the object due to differences in the refractive index of different materials.

The acquisition of X-ray dark-field and phase contrast images relies on a grating interferometer arrangement, that is used to differentiate between the attenuation of radiation, small-angle scattering and refraction. Thus, imaging with an interferometer provides three independent images: conventional attenuation, dark-field and phase contrast. The three imaging modalities are intrinsically perfectly registered. The information provided by X-ray dark-field and phase contrast can be used for diagnostic purposes.

Thus an X-ray dark-field and phase contrast imaging system is based on an interferometry arrangement, that can also acquire x-ray attenuation images. The system is capable of imaging the spatial distribution of attenuation of, or in, an object and also capable of imaging for the spatial distribution of refraction (phase contrast imaging) and also capable of imaging for the spatial distribution of small angle scattering (dark-field imaging). The system has a grating based interferometer that can be scanned across a stationary X-ray detector, or if the gratings are big enough to cover the whole area of the detector no scanning is required. In an example, the interferometer arrangement comprises three grating structures G0, G1 and G2, although in other examples a two grating interferometer (having only a gratings G0 and G1 or G1 and G2) can be used.

Thus looking at the lung for example and dark-field imaging, dark-field contrast is ideally only generated by small-angle scattering caused by the multitude of air-tissue interfaces in the lung. In order to maximize the diagnostic benefit of dark-field imaging, it is then desired to eliminate other contributions to the dark-field signal. In particular, in the past, correction algorithms for Compton scatter and beam-hardening have been introduced and the artificial signal caused by rapid changes of the differential phase (i.e., within a pixel) was studied — see Koehler et al., "non-Scatter Contributions to the Dark-Field Signal in Differential Phase Contrast Imaging", Proceedings of the XNPIG, 2013.

US 2016/0109387 A1 discloses an image processing method for resolution enhancement of images captured in an interferometer system, required due to finite X-ray source size and detector point spread function.

However, in the new technology of X-ray dark field and/or X-ray phase contrast imaging, it is required to make further developments to improve these imaging modalities.

SUMMARY OF THE INVENTION

It would be advantageous to improve the technologies of dark-field and phase contrast X-ray imaging.

The object of the present invention is solved with the subject matter of the independent claims, wherein further embodiments are incorporated in the dependent claims. It should be noted that the following described aspects and examples of the invention apply also to the apparatus for processing of data acquired by a dark-field and/or phase contrast X-ray imaging system, the system for dark-field or phase contrast X-ray imaging, the method for processing of data acquired by a dark-field and/or phase contrast X-ray imaging system, as well as for the computer program element and computer readable medium.

According to a first aspect, there is provided an apparatus for processing of data acquired by a dark-field and/or phase contrast X-ray imaging system. The apparatus comprises:

an input unit; and
a processing unit.

The input unit is configured to provide the processing unit with blank scan fringe data acquired by a dark-field and/or phase contrast X-ray imaging system comprising an interferometry arrangement and detector. The input unit is configured to provide the processing unit with sample scan fringe data acquired by the dark-field and/or phase contrast X-ray imaging system with an object to be imaged positioned within the dark-field and/or phase contrast X-ray imaging system. The processing unit is configured to pre-process the blank scan fringe data to determine pre-processed blank scan fringe data comprising utilization of an effective point spread function "PSF" that has been determined for the dark-field and/or phase contrast X-ray imaging system. The processing unit is configured to pre-process the sample scan fringe data to determine pre-processed sample scan fringe data, comprising utilization of the effective point spread function "PSF".

In other words, fringe data from a dark-field and/or phase contrast X-ray imaging system are acquired when an object is present and when the object is not present. This data would normally be processed to determine a phase contrast image and a dark-field image of the object as well as an attenuation image. However, it has been established by the inventors that cross-talk between detector channels and scatter within the imaging system, that can be described as an effective point spread function for the imaging system, not only leads to a reduction in spatial resolution in the image of the object, but for the phase contrast image and the dark-field image also leads to the introduction of spurious image features. Thus, by correcting the fringe data in the blank fringe data and in the object fringe data, prior to phase retrieval, the corrected fringe data can be used in a normal phase retrieval process and the resultant phase contrast and dark-field images can be reconstructed without the spurious features.

In an example, determination of the pre-processed blank scan fringe data comprises utilization of the effective PSF to high pass filter the blank scan fringe data and wherein determination of the pre-processed sample scan fringe data comprises utilization of the effective PSF to high pass filter the sample scan fringe data.

In an example, determination of the pre-processed blank scan fringe data comprises a deconvolution of the effective PSF and determination of the pre-processed sample scan fringe data comprises a deconvolution of the effective PSF.

In an example, the processing unit is configured to determine a dark-field image of the object and/or a phase contrast image of the object. The determination of the dark-field image of the object and/or a phase contrast image of the object comprises application of a phase retrieval algorithm to the pre-processed blank scan fringe data and to the pre-processed sample scan fringe data.

In an example, determination of the effective PSF comprises utilization of calibration scan data acquired by the dark-field and/or phase contrast X-ray imaging system when a calibration object was positioned within the dark-field and/or phase contrast X-ray imaging system.

In an example, the calibration object comprises a structure configured to block transmission of X-rays of the dark-field and/or phase contrast X-ray imaging system.

In an example, determination of the effective PSF comprises a comparison of an intensity profile of the acquired calibration scan data with an ideal intensity profile.

In an example, determination of the effective PSF comprises modelling of data acquisition by the dark-field and/or phase contrast X-ray imaging system.

According to a second aspect, there is provided a system for dark-field and/or phase contrast X-ray imaging. The system comprises:
- an x-ray source;
- an interferometry arrangement;
- a detector; and
- an apparatus for processing of data acquired by a dark-field and/or phase contrast X-ray imaging system according to the first aspect.

According to a third aspect, there is provided a method for pre-processing of data acquired by a dark-field and/or phase contrast X-ray imaging system, the method comprising:
a) providing a processing unit with blank scan fringe data acquired by a dark-field and/or phase contrast X-ray imaging system comprising an interferometry arrangement and detector;
b) providing the processing unit with sample scan fringe data acquired by the dark-field and/or phase contrast X-ray imaging system, wherein an object to be imaged is positioned within the dark-field and/or phase contrast X-ray imaging system;
c) pre-processing by the processing unit the blank scan fringe data to determine pre-processed blank scan fringe data, the pre-processing comprising utilizing an effective point spread function "PSF", wherein the effective PSF has been determined for the dark-field and/or phase contrast X-ray imaging system; and
d) pre-processing by the processing unit the sample scan fringe data to determine pre-processed sample scan fringe data, wherein the pre-processing comprises utilizing the effective PSF.

In an example, the method comprises step e) determining by the processing unit a dark-field image of the object and/or a phase contrast image of the object, the determining comprising applying a phase retrieval algorithm to the pre-processed blank scan fringe data and to the pre-processed sample scan fringe data.

In an example, determination of the effective PSF comprises utilizing calibration scan data acquired by the dark-field and/or phase contrast X-ray imaging system, wherein a calibration object was positioned within the dark-field and/or phase contrast X-ray imaging system.

In an example, determination of the effective PSF comprises comparing an intensity profile of the acquired calibration scan data with an ideal intensity profile.

In an example, determination of the effective PSF comprises modelling of data acquisition by the dark-field and/or phase contrast X-ray imaging system.

According to another aspect, there is provided a computer program element controlling apparatus and/or system as previously described which, if the computer program element is executed by a processing unit, is adapted to perform the method steps as previously described.

According to another aspect, there is provided a computer readable medium having stored computer element as previously described.

The computer program element, can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
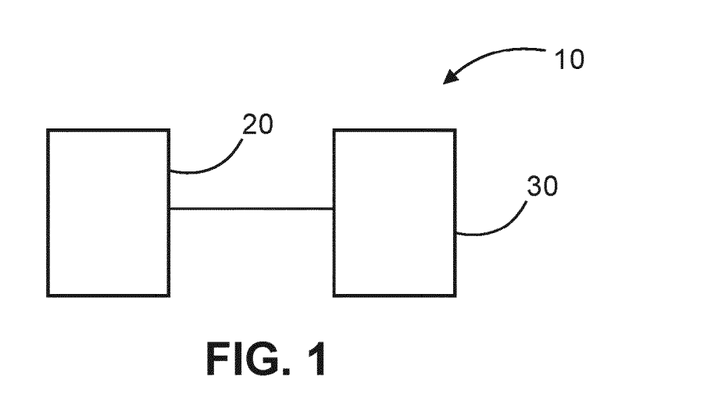
FIG. 1 shows a schematic set up of an example of an apparatus for processing of data acquired by a dark-field and/or phase contrast X-ray imaging system.

FIG. 1 shows schematically an example of an apparatus 10 for processing of data acquired by a dark-field and/or phase contrast X-ray imaging system. The apparatus 10 comprises an input unit 20, and a processing unit 30. The input unit is configured to provide the processing unit with blank scan fringe data acquired by a dark-field and/or phase contrast X-ray imaging system comprising an interferometry arrangement and detector. The input unit is also configured to provide the processing unit with sample scan fringe data acquired by the dark-field and/or phase contrast X-ray imaging system, with an object to be imaged positioned within the dark-field and/or phase contrast X-ray imaging system. The processing unit is configured to pre-process the blank scan fringe data to determine pre-processed blank scan fringe data comprising utilization of an effective point spread function "PSF". The effective PSF has been determined for the dark-field and/or phase contrast X-ray imaging system. The processing unit is configured to pre-process the sample scan fringe data to determine pre-processed sample scan fringe data, comprising utilization of the effective point spread function "PSF.

According to an example, determination of the pre-processed blank scan fringe data comprises utilization of the effective PSF to high pass filter the blank scan fringe data and determination of the pre-processed sample scan fringe data comprises utilization of the effective PSF to high pass filter the sample scan fringe data.

According to an example, determination of the pre-processed blank scan fringe data comprises a deconvolution of the effective PSF and determination of the pre-processed sample scan fringe data comprises a deconvolution of the effective PSF.

According to an example, the processing unit is configured to determine a dark-field image of the object and/or a phase contrast image of the object. The determination of the dark-field image of the object and/or the phase contrast image of the object comprises application of a phase retrieval algorithm to the pre-processed blank scan fringe data and to the pre-processed sample scan fringe data.

According to an example, determination of the effective PSF comprises utilization of calibration scan data acquired by the dark-field and/or phase contrast X-ray imaging system when a calibration object was positioned within the dark-field and/or phase contrast X-ray imaging system.

According to an example, the calibration object comprises a structure configured to block transmission of X-rays of the dark-field and/or phase contrast X-ray imaging system.

In an example, the calibration object comprises a metal plate blocking transmission of X-rays of the dark-field and/or phase contrast X-ray imaging system from striking a portion of the detector.

In an example, the calibration object comprises a metal plate covering a portion of the detector.

According to an example, determination of the effective PSF comprises a comparison of an intensity profile of the acquired calibration scan data with an ideal intensity profile.

According to an example, determination of the effective PSF comprises modelling of data acquisition by the dark-field and/or phase contrast X-ray imaging system.

Figure 2:
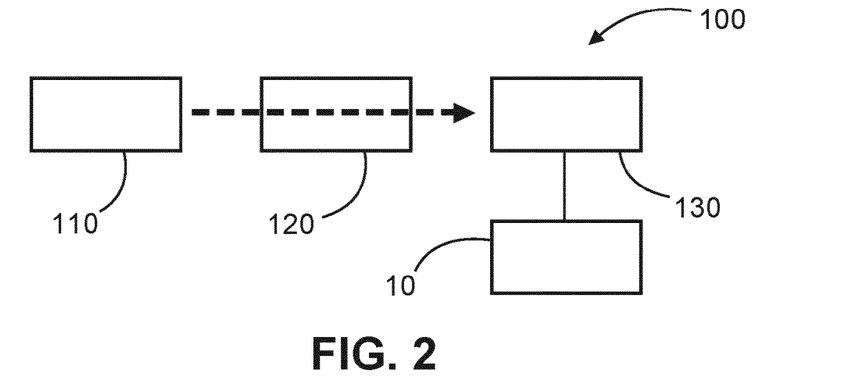
FIG. 2 shows a schematic set up of an example of a system for a dark-field and/or phase contrast X-ray imaging system.

FIG. 2 shows schematically an example of a system 100 for dark-field and/or phase contrast X-ray imaging. The system comprises an x-ray source 110, an interferometry arrangement 120, and a detector 130. The system 100 also comprises an apparatus for processing of data acquired by a dark-field and/or phase contrast X-ray imaging system as described with respect to FIG. 1.

Figure 3:
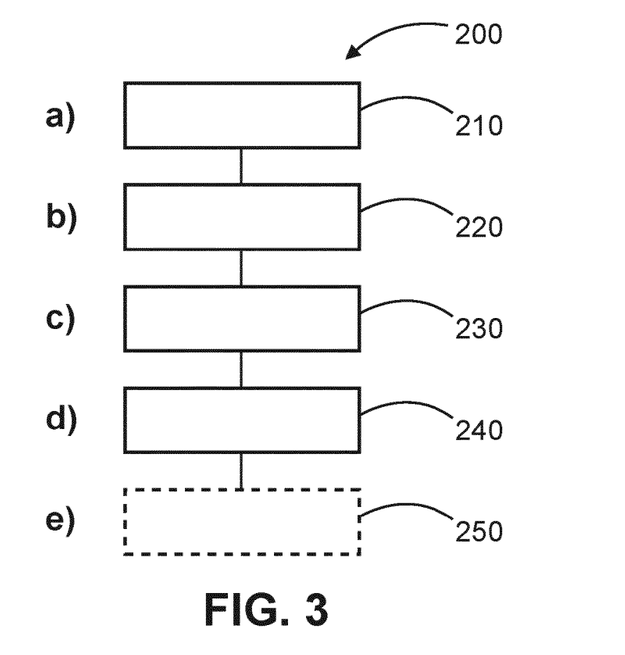
FIG. 3 shows a method for processing of data acquired by a dark-field and/or phase contrast X-ray imaging system.

FIG. 3 shows a method 200 for pre-processing of data acquired by a dark-field and/or phase contrast X-ray imaging system in its basic steps. Essential steps are represented as solid boxes and optional steps are represented as a dashed box and described in the examples below. The method 200 comprises:

in a providing step 210, also referred to as step a), providing a processing unit with blank scan fringe data acquired by a dark-field and/or phase contrast X-ray imaging system comprising an interferometry arrangement and detector;

in a providing step 220, also referred to as step b), providing the processing unit with sample scan fringe data acquired by the dark-field and/or phase contrast X-ray imaging system, wherein an object to be imaged is positioned within the dark-field and/or phase contrast X-ray imaging system;

in a pre-processing step 230, also referred to as step c), pre-processing by the processing unit the blank scan fringe data to determine pre-processed blank scan fringe data, the pre-processing comprising utilizing an effective point spread function "PSF", wherein the effective PSF has been determined for the dark-field and/or phase contrast X-ray imaging system; and in a pre-processing step 240, also referred to as step d), pre-processing by the processing unit the sample scan fringe data to determine pre-processed sample scan fringe data, wherein the pre-processing comprises utilizing the effective PSF.

In an example, step c) comprises utilizing the effective PSF to high pass filter the blank scan fringe data and step d) comprises utilizing the effective PSF to high pass filter the sample scan fringe data.

In an example, step c) comprises de-convolving the effective PSF.

According to an example, the method comprises step e) also referenced as step 250 determining by the processing unit a dark-field image of the object and/or a phase contrast image of the object, the determining comprising applying a phase retrieval algorithm to the pre-processed blank scan fringe data and the pre-processed sample scan fringe data.

According to an example, determination of the effective PSF comprises utilizing calibration scan data acquired by the dark-field and/or phase contrast X-ray imaging system, wherein a calibration object was positioned within the dark-field and/or phase contrast X-ray imaging system.

In an example, the calibration object comprises a structure configured to block transmission of X-rays of the dark-field and/or phase contrast X-ray imaging system.

In an example, the calibration object comprises a metal plate covering a portion of the detector.

According to an example, determination of the effective PSF comprises comparing an intensity profile of the acquired calibration scan data with an ideal intensity profile.

According to an example, determination of the effective PSF comprises modelling of data acquisition by the dark-field and/or phase contrast X-ray imaging system.

In an example, the modelling comprises calculating calibration scan data acquired by a model of the dark-field and/or phase contrast X-ray imaging system, wherein the calculated data relates to a modelled calibration object positioned within the model of the dark-field and/or phase contrast X-ray imaging system.

In an example, determining the effective PSF comprises comparing an intensity profile of the calculated calibration scan data with an ideal intensity profile.

The apparatus and method for processing of data acquired by a dark-field and/or phase contrast X-ray imaging system, and the system for dark-field or phase contrast X-ray imaging are now described with respect to specific embodiments, where reference is made to FIGS. 4-9.

Figure 9:
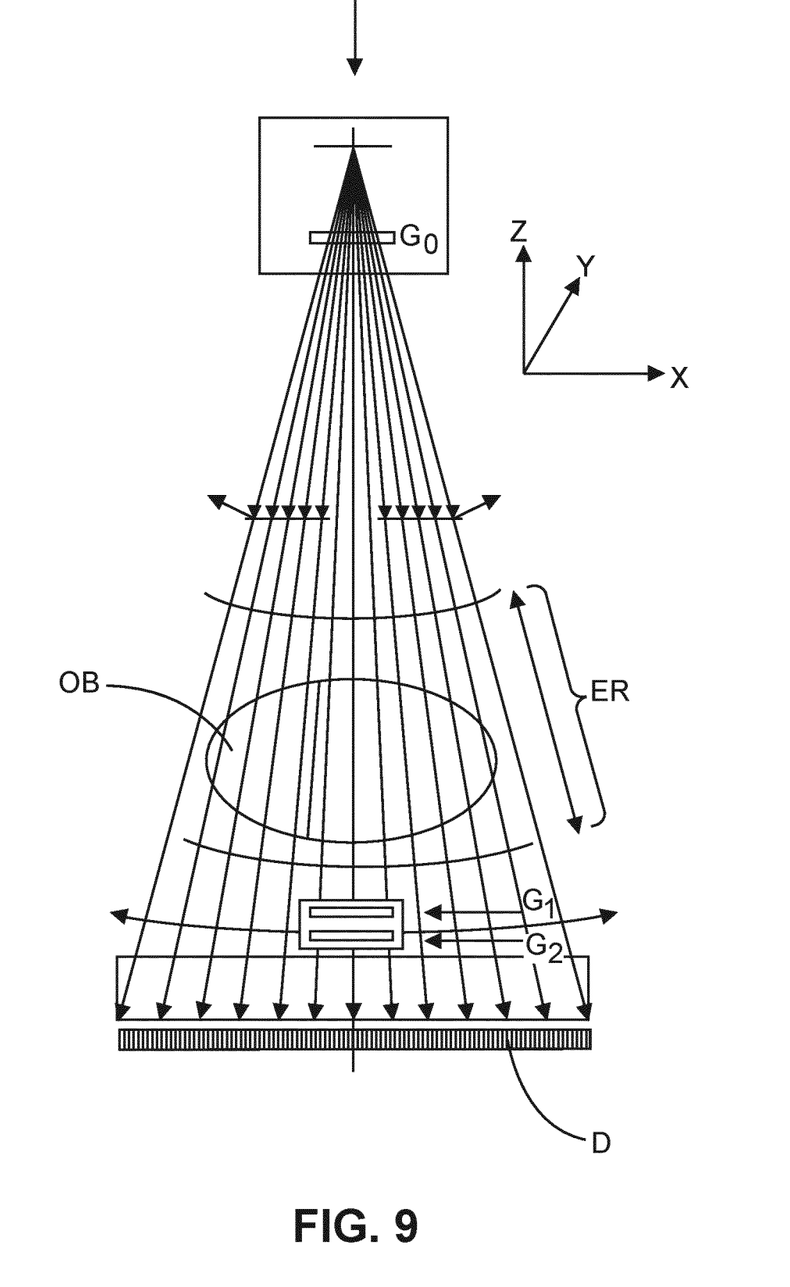
FIG. 9 shows a schematic set up of an example of a phase contrast and/or dark-field imaging system.

For the acquisition of the dark-field and phase contrast data, as well as the attenuation data, a two (Talbot type) or three-grating (Talbot-Lau type) interferometer is introduced into the X-ray beam, normally termed G0, G1 and G2 gratings. An exemplar system is shown in FIG. 9, where typically G0 and G2 are absorber gratings and G1 is a phase grating, and where an object OB is placed within an examination region ER. The source grating G0, can be used to make radiation from the source more coherent but is not always necessary, and gratings G1 and G2 are normally termed phase and analyzer gratings. Subsequently, for a so-called full field system, one of the two gratings G1 or G2 is moved perpendicular to the grating lamellae relative to the other gratings in a number of steps (so-called stepping), and if the source grating G0 is utilized it can be this grating that is stepped laterally (where laterally means perpendicular to the grating direction). Thereby, for each new grating position an image is recorded on the detector D. Comparison of the image sequence acquired with and without a sample in the beam, allows to calculate the three imaging signals: transmission or attenuation (conventional X-ray image), phase contrast image, and dark-field image. These gratings generate a fringe pattern on top of the conventional transmission image, and for example the dark-field signal is calculated as the loss of contrast of this fringe pattern. The fringe-pattern, which is analyzed in dark-field and phase contrast imaging, is a fine structure in the micrometer range. Using an analyzer grating with the same periodicity, a Moire-pattern can be measured with the detector. Any movement of one or more interferometer components, such as the analyzer grating, in this length scale changes the phase of the Moire-pattern. Instead of using a full-field system and phase stepping, a scanning type of system can be used as described e.g. in US 9959640 B2.

Thus, a sample or object, the body in FIG. 9, modulates attenuation, refraction, and small angle scattering information onto the radiation. To separate phase information from other contributions to the signal, such as attenuation by the sample, inhomogeneous illumination or imperfections of the gratings, a phase "stepping" approach is utilized. One of the gratings (either G1 or G2 - or G0 if present) is scanned along the transverse direction over at least one period of the grating, and for every point of the scan an image is taken. The resultant phase contrast, dark-field, and attenuation data then oscillates sinusoidal, with and without the sample, and this can be utilized to determine the dark-field, phase contrast and attenuation images. Further detail on the standard phase stepping approach can be found in the paper by Weitkamp et al, Optics Express, Vol. 13, No. 16, (2005) 6296-6304.

Standard phase retrieval is done on a per-pixel basis, using the model $$f_{ij} = I_i T_i \left(1 + V_i D_i \cos(\alpha_i + \beta_i + \phi_j)\right) \qquad (1)$$

where $I_i$, $V_i$, and $\alpha_i$ are blank scan intensity, fringe visibility, and fringe phase for pixel i, respectively. Variables $T_i$, $D_i$, and ? $2_i$ denote the transmission, dark-field, and phase shift created by the object. Finally, ??$_j$ denotes the phase shift induced by the grating motion.

Figure 4:
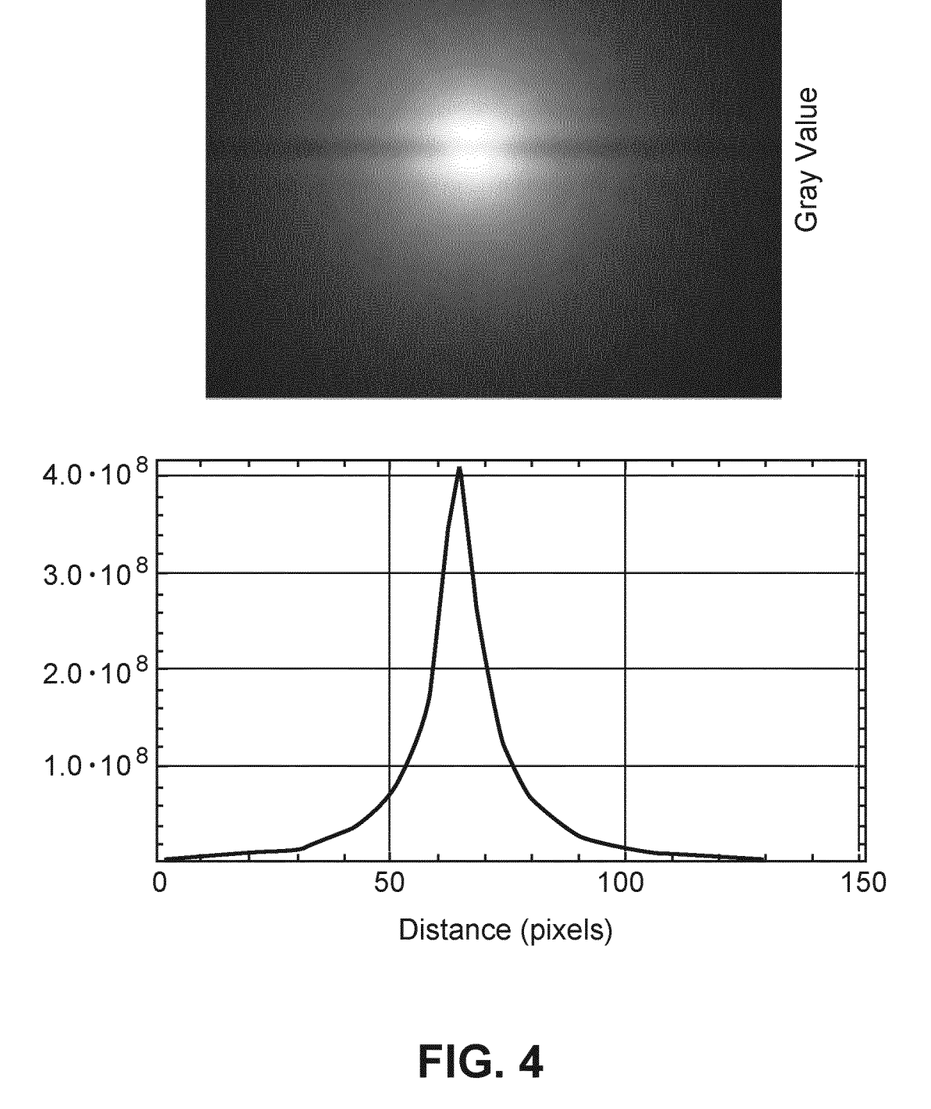
FIG. 4 illustrates the contribution of Compton and Rayleigh scattering in a G2 grating of a dark-field and phase contrast X-ray imaging system as an effective PSF, where on the upper part a 2D illustration shows the asymmetry in the xy-direction, and on the lower part a line plot through the estimated G2 scatter contribution is shown.

It is known that crosstalk occurs in such an imaging system. The term crosstalk is used here in a very broad sense. It covers the "traditional" concept of crosstalk, like optical crosstalk in the scintillator or electronic crosstalk in the detector electronics. However, it also covers backscatter effects (photons passing once the scintillation layer, being Compton-scattered in the detector electronics or cover back into the scintillator and being detected then) and scattering by the G2 grating. All these effects have in common that they can be described by an effective point spread function (PSF). For the case of scattering in G2, the corresponding PSF is illustrated in FIG. 4. FIG. 4 illustrates the contribution of Compton and Rayleigh scattering in G2 to the effective PSF for such a dark-field and phase contrast system. Top: 2D illustration showing the asymmetry in xy-direction. Bottom: a line plot through the estimated G2 scatter contribution is shown.

Within the community working on this new imaging modality, so far it has been a common (unspoken) belief that a non-perfect PSF leads to just a loss in spatial resolution in each of the three images generated by the system.

However, the inventors established that crosstalk between detector channels can also cause an artificial dark-field signal (and phase contrast signal) in certain situations, and the apparatus, method and system described here addresses this.

The following details the fundamentals behind the new technological development for improving X-ray dark-field and phase contrast imaging, where a detailed analysis of the effect of a non-perfect PSF is presented.

Consider two pixels which suffer from crosstalk. This is modelled by a signal exchange by a fraction a between the channels, where equation (1) has been utilized:

$$f_{1j} = (1-a)IT_1\left(1 + VD_1\cos(\alpha_1 + \beta_1 + \phi_j)\right) + \\ aIT_2\left(1 + VD_2\cos(\alpha_2 + \beta_2 + \phi_j)\right)$$

for the sake of compactness, it is assumed that the blank scan parameters I and V are the same for the two pixels. By means of basic calculus, this signal model can be transformed again into the standard form (Eq. 1) as $$f_{1j} = I\,\hat{T}_1(1 + V\hat{D}_1\cos(\hat{\alpha}_1 + \phi_j))$$

With $$\hat{T}_1 = \frac{(1-a)T_1 + aT_2}{}$$

$$\hat{D}_1 = \frac{\sqrt{\left((1-a)T_1D_1\right)^2 + (aT_2D_2)^2 + 2a(1-a)T_1T_2D_1D_2\cos(\alpha_1 + \beta_1 - \alpha_2 - \beta_2)}}{(1-a)T_1 + aT_2}$$

$$\hat{\alpha}_1 = \arctan\frac{(1-a)T_1D_1\cos(\alpha_1 + \beta_1) + aT_2D_2\cos(\alpha_2 + \beta_2)}{(1-a)T_1D_1\sin(\alpha_1 + \beta_1) + aT_2D_2\sin(\alpha_2 + \beta_2)}$$

Thus, the inventors established that the intuitive expectation that the crosstalk just produces a low-pass filtering on the three images is incorrect. It holds true only for the transmission image. For the dark-field image, there are only certain cases (e.g. $\alpha_1 + \beta_1 - \alpha_2 - \beta_2 = 0$ and $T_1 = T_2$, which result in the same low-pass filtering effect on the dark-field image, i.e.

$$\hat{D}_1 = (1-a)D_1 + aD_2$$

. In the general case, the dependency of $$\hat{D}_1$$

on $T_2$ and $D_2$ is modulated by difference between $\alpha_1 + \beta_1$ and $\alpha_2 + \beta_2$, i.e. the difference in the actual fringe phase between the two pixels plays an important role and a detailed analysis shows that the crosstalk induced artificial dark-field signal is minimal if the actual fringe phases are the same. Note that this insight is of particular importance for a slot-scanning dark-field system as this is designed to have a spatially high-frequent fringe pattern. Consequently, slot-scanning systems will suffer more from this crosstalk effect than full-field systems.

The new developed technology handles this problem and compensates for crosstalk in a pre-processing step before the actual phase retrieval. The pre-processing step, which can be termed resolution recovery by un-folding the effective PSF or PSF-deconvolution, is applied to both the blank scan and the sample scan. Instead of a full de-convolution of the PSF, which will substantially increase the noise, only correction for the long ranging tail of the PSF can be conducted.

The following provides details of an example of how the effective PSF for a dark-field and phase contrast imaging system can be determined, and how PSF-deconvolution can be performed.

PSF Determination

The measured intensity $I_{meas}$ is a sum of the true, non PSF affected intensity distribution $I_{ideal}$ and a redistribution $I_{PSF}$ due to a finite width of the Point-Spread-Function (PSF):

$$I_{meas} = I_{ideal} + I_{PSF}$$

Now if a highly absorbing tungsten plate is placed directly onto a part of the detector, the ideal intensity behind that plate would be $I_{ideal} = 0$, and for the uncovered part of the detector it would be the normal signal. The measured intensity however behind the plate is larger than this, due to both noise and the PSF. From other measurements, it can be established that noise is dominant when there are less than about 10 counts. For higher intensities, above about 50 counts, the noise averages to zero when taking the mean over many pixels. Thus, it can be assumed for high enough intensities behind the tungsten plate, that the measured intensity is due to the PSF only. These numbers apply to a specific detector and will be different for different detector. For instance, for a photon counting detector, no electronic noise is present and any count can be considered as signal.

This measured intensity can then be used to find a kernel for the PSF:

$$I_{meas} = I_{ideal} + \text{PSF} * I_{ideal} = I_{ideal} + A \, I_{ideal}$$

where "*" denotes a convolution and A denotes the operator that applies the convolution with PSF to the ideal intensities $I_{ideal}$. Of course, the PSF may be spatially variant, for instance because the x-rays hit the detector at different angles in the center of the (usually flat) detector and the edge. In this case, $I_{PSF}$ cannot be written as a simple space invariant convolution but the PSF kernel becomes space-variant. Still it can be written as a linear operator A applied to the ideal measurement.

Therefore, the measured intensity behind the tungsten plate is fitted with a least-squares fit based on the whole measured intensity distribution for the covered and uncovered parts of the detector, with the PSF kernel as fit parameters. Here, a model for the PSF is used as follows:

$$\text{PSF} = \text{PSF}(r) = \frac{s}{r^2} e^{-\alpha r}$$

In this model the processes generating the PSF are considered to be radially symmetric and generate photons isotropically in all directions ($1/r^2$) and that the generated photons are absorbed following an exponential law, as in the law of Beer-Lambert. The two parameters s and $\alpha$ correspond to the overall strength of the PSF and the attenuation of the generated photons, respectively.

Figure 5:
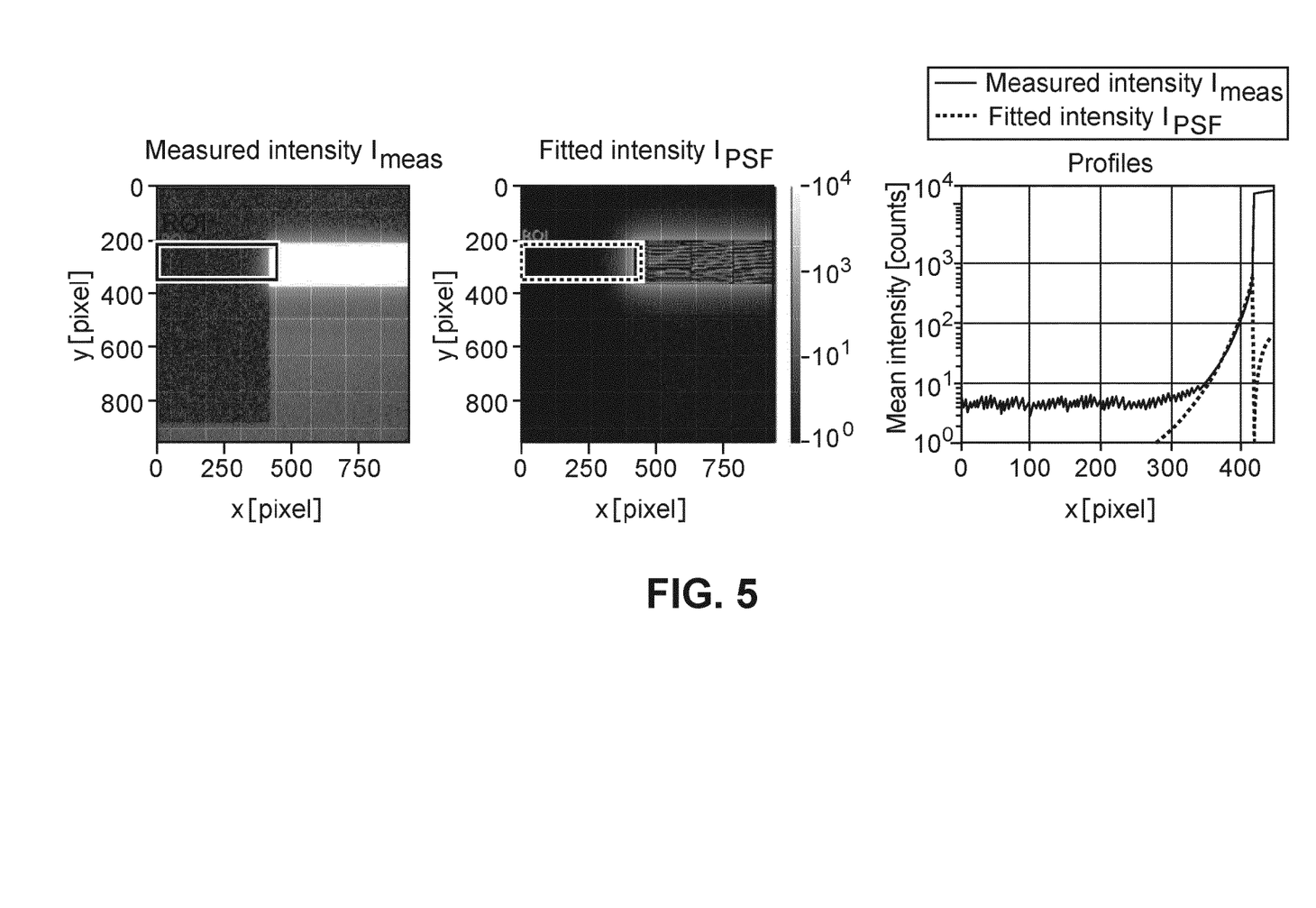
FIG. 5 shows an example measured exposure of a dark-field and phase contrast X-ray imaging system with a tungsten plate placed over a part of the detector, and shows an example of data that has been fitted to the measured data where an effective PSF has been utilized, and also shown is a plot in the x-direction for the measured data and the fitted data.

FIG. 5 shows on the left image one exemplary exposure from the dark-field system and phase contrast imaging system, with a tungsten plate over the left side of the detector. The middle image shows the intensity obtained from the fit to the measured data. The relevant area for fitting was hereby the region behind the tungsten, and that close to the tungsten border. In the region behind the tungsten, but far away from the border, the measured intensity is mainly due to electronic noise and thus not relevant for PSF-fitting. In the region without tungsten, the intensity is mainly due to the direct beam. However, in the area behind the tungsten plate but close to the border with the uncovered part of the detector the signal is above the electronic noise level, and this is due to the PSF.

Figure 6:
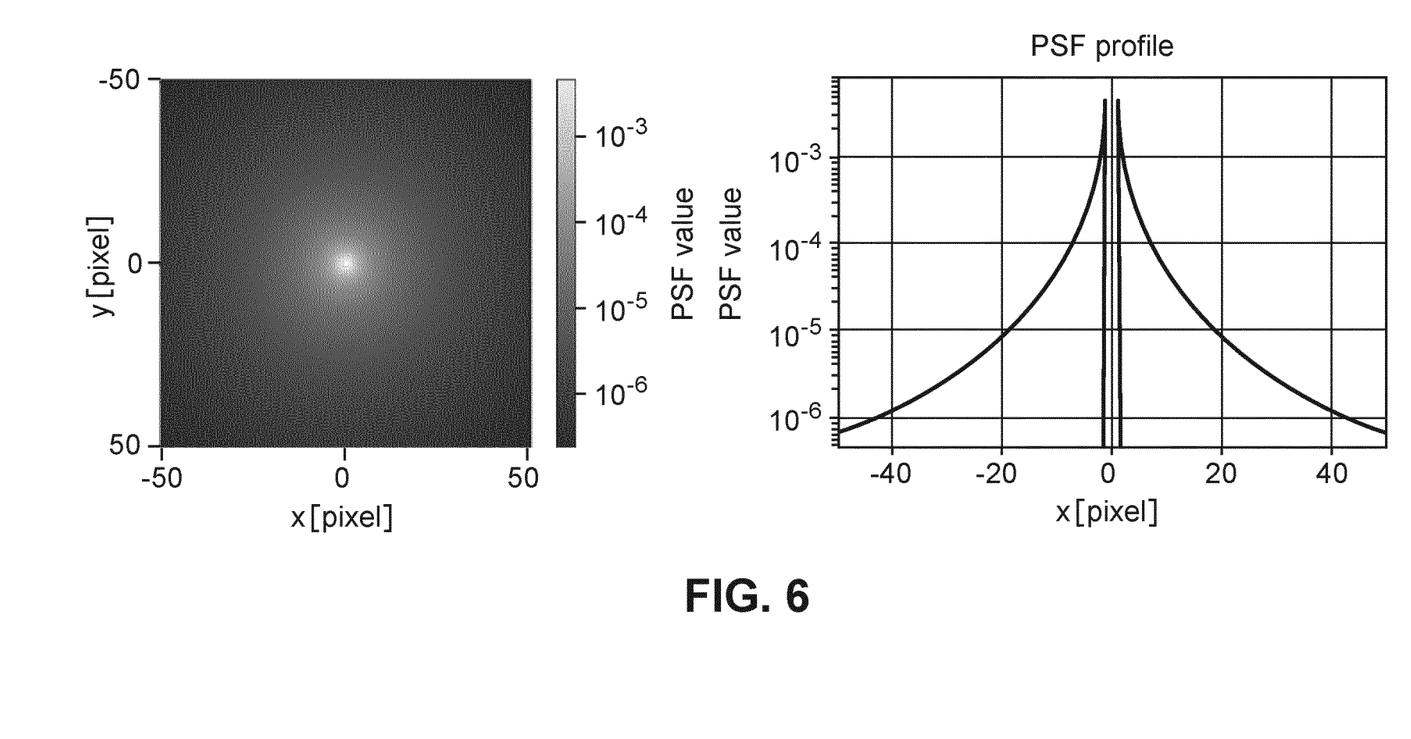
FIG. 6 shows the effective PSF determined for the dark-field and phase contrast X-ray imaging system used to obtain the data shown in FIG. 5.

Therefore, the ideal signal would be an abrupt fall from the uncovered detector signal to the electronic noise signal when crossing the tungsten plate border. The above equation is used to fit to the measured data, and as detailed above this is used to determine the PSF. Continuing with FIG. 5 the right part shows profiles in the x-direction within the region-of-interest (ROI) in both the measured data image and the fitted data image, showing that the fit matches the measured intensity well in the relevant area. FIG. 6 shows the PSF determined in this manner.

PSF-Deconvolution

As discussed above. the measured intensity $I_{meas}$ is a sum of the true, non PSF affected intensity distribution $I_{ideal}$ and a redistribution $I_{PSF}$ due to a finite width of the Point-Spread-Function (PSF):

$$I_{meas} = I_{ideal} + I_{PSF}$$

The algorithm presented here recovers the true intensity distribution from the measurement, using a previously determined PSF — see above for example.

The redistribution can be, by definition, calculated from the true intensity and the PSF, with * symbolizing a convolution:

$$I_{meas} = I_{PSF} = PSF * I_{ideal} = I_{ideal} + A\, I_{ideal}$$

Using this, $I_{ideal}$ can now be calculated:

$$I_{meas} = (\mathbb{I} + A) I_{ideal}$$

$$a?1 I_{ideal} = (\mathbb{I} + A)^{-1} I_{meas}$$

Where $\mathbb{I}$ is the identity operator.

To find $(\mathbb{I} - A)^{-1}$ the so-called Neumann-Series can be used:

$$(\mathbb{I} - A)^{-1} = \sum_{n=0}^{\infty} A^n$$

Therefore, $$I_{ideal} = \sum_{n=0}^{\infty} (-A)^n I_{meas} = (\mathbb{I} - A + A^2 - A^3 \ldots) I_{meas}$$

Here, $A^n$ symbolizes applying the operator n times.

Since the finite PSF only redistributes the detector counts, $\sum I_{PSF} = 0$ holds. This means that also the PSF kernel is normalised such that $\sum PSF = 0$, by setting the value of the central pixel to the negative sum of all other pixels in the kernel. The kernel use for deconvolution of images is that shown in FIG. 6.

Figure 7:
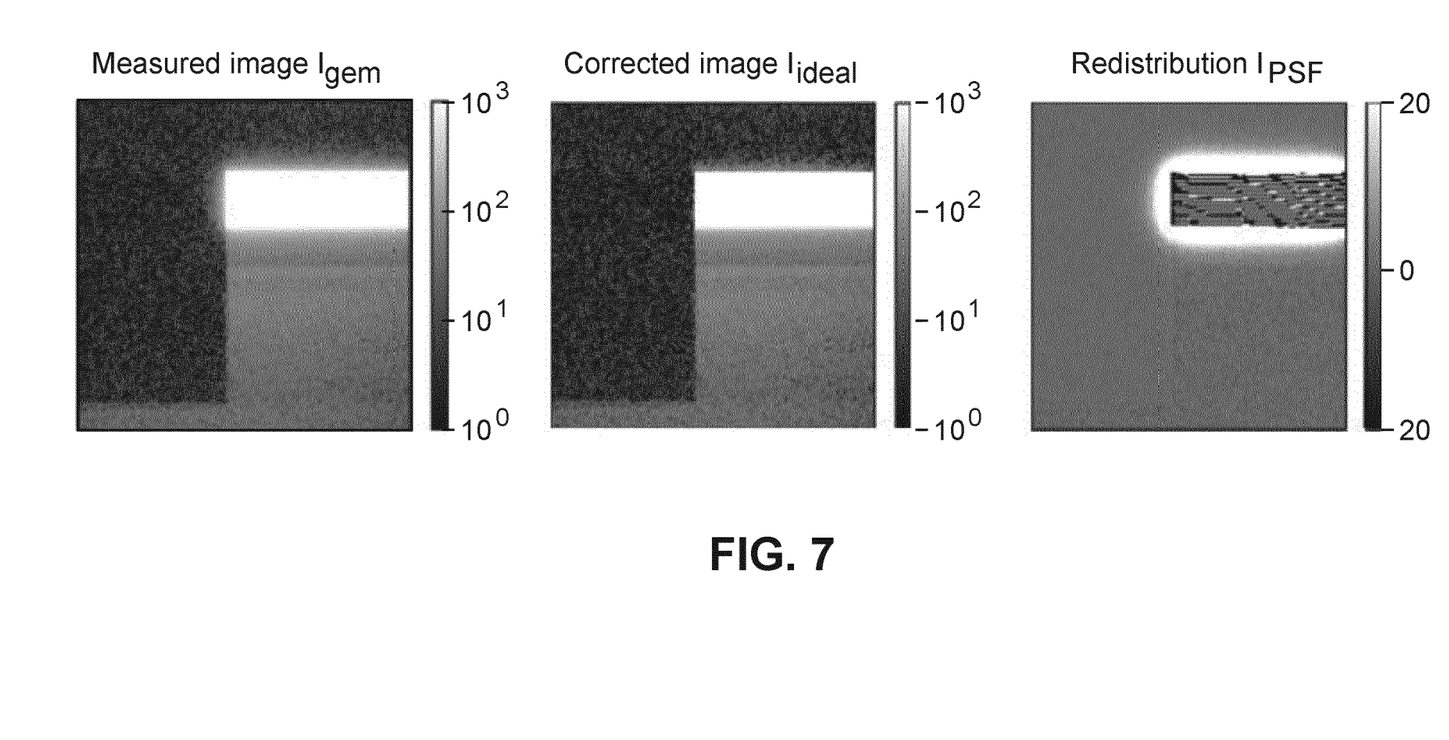
FIG. 7 shows the measured exposure of the dark-field and phase contrast X-ray imaging system with the tungsten plate placed over a part of the detector as shown in FIG. 5, and shows the PSF-corrected intensity distribution, and shows a difference between the two representing a redistribution of intensity.

FIG. 7 depicts an exemplary shot of a phantom measurement with a highly absorbing tungsten plate on the left side of the detector. On the left, the measured intensity distribution $I_{meas}$ is shown, in the middle the PSF-corrected intensity distribution $I_{ideal}$ is shown, and on the right, the difference between these two, i. e. the redistribution of intensity $I_{PSF}$ is shown. While there is very little effect on the homogeneously irradiated areas, the regions around the strongly absorbing features are clearly less blurry in the corrected images.

Figure 8:
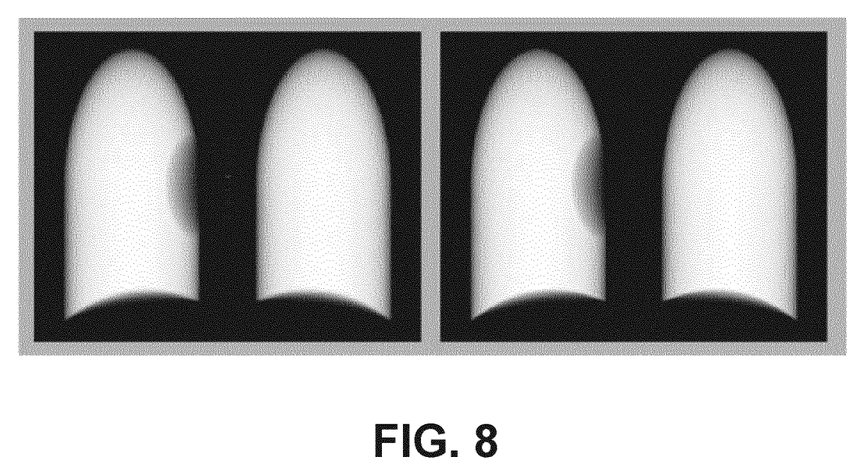
FIG. 8 shows on the left a simulation of a dark-field image acquired by the dark-field and phase contrast X-ray imaging system of FIGS. 5-7 that has not been corrected for an effective PSF and on the right a simulation is shown where the acquired data were corrected before application of phase retrieval.

This improvement in the regions around strongly absorbing features, can be seen in FIG. 8. This illustrates utilization of the above algorithm, as utilized in the apparatus, system and method described here, on clinical chest dark-field imaging, where simulated data are shown. The left image shows a simulated dark-field image without PSF unfolding with an artificial signal by the ribs, which is reduced by the above described algorithm, demonstrated on the right hand simulated image.

In the above example of the determination of the effect point spread function (PSF) the tungsten plate was directly placed adjacent to the detector to block part of the detector. This however is just one example, and the tungsten plate could have been placed in the normal object position such that again a portion of detector is blocked from receiving x-rays. In this latter example, the effective point spread function will account for scatter within the interferometric system itself (interferometric arrangement crosstalk) as well as crosstalk between detector channels. The above example however enables the skilled person to understand how an effective point spread function can be determined and applied to improve dark-field and phase contrast imagery.

In another exemplary embodiment, a computer program or computer program element is provided that is characterized by being configured to execute the method steps of the method according to one of the preceding embodiments, on an appropriate apparatus/system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are recited in mutually different dependent claims does not indicate that a combination of these measures cannot be used to advantage. Any reference signs in the claims should not be construed as limiting the scope.

The invention claimed is:

1. Apparatus for processing of data acquired by a dark-field and/or phase contrast X-ray imaging system, the apparatus comprising:
   input unit; and
   processing unit;
   wherein the input unit is configured to provide the processing unit with blank scan fringe data acquired by a dark-field and/or phase contrast X-ray imaging system comprising an interferometry arrangement and detector;
   wherein the input unit is configured to provide the processing unit with sample scan fringe data acquired by the dark-field and/or phase contrast X-ray imaging system, wherein an object to be imaged is positioned within the dark-field and/or phase contrast X-ray imaging system;
   wherein the processing unit is configured to pre-process the blank scan fringe data to determine pre-processed blank scan fringe data comprising utilization of an effective point spread function (PSF);
   wherein the processing unit is configured to pre-process the sample scan fringe data to determine pre-processed sample scan fringe data, comprising utilization of the effective "PSF"; and
   wherein the effective PSF has been determined for the dark-field and/or phase contrast X-ray imaging system.

2. Apparatus according to claim 1, wherein determination of the pre-processed blank scan fringe data comprises utilization of the effective PSF to high pass filter the blank scan fringe data and wherein determination of the pre-processed sample scan fringe data comprises utilization of the effective PSF to high pass filter the sample scan fringe data.

3. Apparatus according to claims 1, wherein determination of the pre-processed blank scan fringe data comprises a deconvolution of the effective PSF and wherein determination of the pre-processed sample scan fringe data comprises a deconvolution of the effective PSF.

4. Apparatus according to claims 1, wherein the processing unit is configured to determine a dark-field image of the object and/or a phase contrast image of the object, the determination comprising application of a phase retrieval algorithm to the pre-processed blank scan fringe data and to the pre-processed sample scan fringe data.

5. Apparatus according to claims 1, wherein determination of the effective PSF comprises utilization of calibration scan data acquired by the dark-field and/or phase contrast X-ray imaging system when a calibration object was positioned within the dark-field and/or phase contrast X-ray imaging system.

6. Apparatus according to claim 5, wherein the calibration object comprises a structure configured to block transmission of X-rays of the dark-field and/or phase contrast X-ray imaging system.

7. Apparatus according to claims 5, wherein determination of the effective PSF comprises a comparison of an intensity profile of the acquired calibration scan data with an ideal intensity profile.

8. Apparatus according to claims 1, wherein determination of the effective PSF comprises modelling of data acquisition by the dark-field and/or phase contrast X-ray imaging system.

9. A system for dark-field and/or phase contrast X-ray imaging, the system comprising:
   an x-ray source;
   an interferometry arrangement;
   a detector; and
   an apparatus for processing of data acquired by the system, the apparatus comprising:
      an input unit; and
      a processing unit;
      wherein the input unit is configured to provide the processing unit with blank scan fringe data acquired by a dark-field and/or phase contrast X-ray imaging system comprising an interferometry arrangement and detector;
      wherein the input unit is configured to provide the processing unit with sample scan fringe data acquired by the dark-field and/or phase contrast X-ray imaging system, wherein an object to be imaged is positioned within the dark-field and/or phase contrast X-ray imaging system;
      wherein the processing unit is configured to pre-process the blank scan fringe data to determine pre-processed blank scan fringe data comprising utilization of an effective point spread function (PSF);
      wherein the processing unit is configured to pre-process the sample scan fringe data to determine pre-processed sample scan fringe data, comprising utilization of the effective PSF; and
      wherein the effective PSF has been determined for the dark-field and/or phase contrast X-ray imaging system.

10. A method for pre-processing of data acquired by a dark-field and/or phase contrast X-ray imaging system, the method comprising:
   providing a processing unit with blank scan fringe data acquired by a dark-field and/or phase contrast X-ray imaging system comprising an interferometry arrangement and detector;
   providing the processing unit with sample scan fringe data acquired by the dark-field and/or phase contrast X-ray imaging system, wherein an object to be imaged is positioned within the dark-field and/or phase contrast X-ray imaging system;
   pre-processing by the processing unit the blank scan fringe data to determine pre-processed blank scan fringe data, the pre-processing comprising utilizing an effective point spread function (PSF), wherein the effective PSF has been determined for the dark-field and/or phase contrast X-ray imaging system; and
   pre-processing by the processing unit the sample scan fringe data to determine pre-processed sample scan fringe data, wherein the pre-processing comprises utilizing the effective PSF.

11. Method according to claim 10, wherein the method comprises determining by the processing unit a dark-field image of the object and/or a phase contrast image of the object, the determining comprising applying a phase retrieval algorithm to the pre-processed blank scan fringe data and the pre-processed sample scan fringe data.

12. Method according to claims 10, wherein determination of the effective PSF comprises utilizing calibration scan data acquired by the dark-field and/or phase contrast X-ray imaging system, wherein a calibration object was positioned within the dark-field and/or phase contrast X-ray imaging system.

13. Method according to claim 12, wherein determination of the effective PSF comprises comparing an intensity profile of the acquired calibration scan data with an ideal intensity profile.

14. Method according to claims 10, wherein determination of the effective PSF comprises modelling of data acquisition by the dark-field and/or phase contrast X-ray imaging system.

* * * * *